United States Patent [19]

Walsh

[11] 4,288,742
[45] Sep. 8, 1981

[54] ELECTRICAL MOISTURE SENSOR

[75] Inventor: John E. Walsh, Box 264, Bradford, Vt. 05033

[73] Assignees: Dartmouth College; John E. Walsh, both of Hanover, N.H. ; part interest to each

[21] Appl. No.: 104,738

[22] Filed: Dec. 18, 1979

[51] Int. Cl.³ .......................................... G01R 27/26
[52] U.S. Cl. .................. 324/61 R; 324/61 P
[58] Field of Search ................. 324/61 P, 61 R, 65 P; 73/73, 74

[56] References Cited

U.S. PATENT DOCUMENTS

| | | | |
|---|---|---|---|
| 2,587,771 | 3/1952 | Schoenbaum et al. | 324/65 P |
| 2,870,404 | 1/1959 | Oxley | 324/65 P |
| 2,975,361 | 3/1961 | Holaday | 324/61 R X |
| 3,803,570 | 4/1974 | Barlow | 324/61 R X |
| 3,882,381 | 5/1975 | Gregory . | |
| 3,986,110 | 10/1976 | Overall et al. . | |
| 4,135,151 | 1/1979 | Rogers et al. . | |
| 4,174,498 | 11/1979 | Preikschat . | |
| 4,181,881 | 1/1980 | Preikschat . | |

FOREIGN PATENT DOCUMENTS 54-115296 9/1979 Japan .................................. 324/61 P
709177 5/1954 United Kingdom .............. 324/61 P

OTHER PUBLICATIONS

Foldvari et al., Capacitive Transducers, Instruments & Control Systems, Nov. 1964, pp. 77-84.

Primary Examiner—Stanley T. Krawczewicz
Attorney, Agent, or Firm—Cushman, Darby & Cushman

[57] ABSTRACT

A moisture sensor including a probe formed with a first ring of spines extending in parallel outward from a base and a second ring of spines extending in parallel outward from the base separated and insulated from the first ring, the spines forming an effective coaxial capacitor and being insertable into material to be sensed and an RC bridge circuit, preferably a Wien bridge connected to the rings to measure the impedance of the material.

4 Claims, 3 Drawing Figures

ELECTRICAL MOISTURE SENSOR

The present invention relates to a sensor for producing a signal indicating the moisture content of material into which spines of the sensor are inserted.

Many applications exist in which it is necessary to accurately ascertain the moisture content of material. For example, knowing the exact moisture content of soil is important in agricultural applications, in waste treatment applications where soil is used for purifying water, for erosion studies, for monitoring earth dams, and for various military applications. Accurately determining the moisture content of grain is another important application. Maintaining accurate records as to the amount of moisture in trees is not only important in preventing forest fires, but also in monitoring the growth of those trees. Many other industrial applications such as curing concrete also require periodic and accurate information as to the moisture content of material.

Typically, moisture sensing devices in the past have included a container into which the material is placed, with plates or the like therein for determining the capacitance of the material placed therein and relating that capacitance to the moisture content. For example, the patent to Mead U.S. Pat. No. 3,209,247 and the patent to Marsh et al U.S. Pat. No. 4,050,016, show typical devices of this sort. These devices are, however, inconvenient to use since they require removing a portion of the material to be tested. Further, removing the material, for example, digging a sample of soil, necessarily changes its density so that the measured results are not necessarily the actual moisture content of the soil before its removal.

Another inaccuracy arises because these devices measure only the capacitance of the soil. In fact, both the resistance and capacitance of the soil vary with moisture and vary independently of each other depending upon soil conditions. The relation of resistance to moisture particularly is non-linear and very difficult to predict for any given composition. Devices which ignore variation of resistance with capacitance necessarily produce an inaccurate indication of moisture content.

The present invention relates to a unique, simple, and effective moisture sensor which can be inserted easily into material to be measured, usually without damage to that material, and which takes into account both resistance and capacitance to produce an accurate indication of moisture content. The sensor includes a probe having at least a single, and preferably a plurality of spines extending outward from a base so that the spines can be inserted into the material. The impedance produced by the material surrounding the spines forms part of an RC bridge, preferably a Wien bridge, which also includes a separate resistor and capacitor. Thus, the impedance of the material, both its capacitance and resistance, are measured to produce signals indicating that impedance. By determining the ratio of the voltages across the RC circuit forming part of the bridge and the RC circuit of the material impedance and determining the resonant frequency, both the resistance and capacitance of the soil can be determined and related to the dielectric constant of the material. From that dielectric constant the soil moisture content can be easily determined according to well known relations.

The present invention also relates to a unique moisture sensor which utilizes a co-axial geometry to accurately define the active volume by minimizing fringe volumes. With sensors of the type which use plates, the fringe capacitances introduce errors since those capacitances vary with the dielectric constant. The co-axial geometry of the present sensor has no such fringe capacitance, except at the ends. According to this improved sensor, a first ring of spines extends outwardly from a base in parallel with a second ring of spines extending outwardly from the base, also in parallel, and within the first ring, separated and insulated electrically therefrom. The two rings thus form an effective coaxial capacitor which can be inserted into the material to be sensed.

Other objects and purposes of the invention will be clear from the following detailed description of the drawings.

DETAILED DESCRIPTION OF THE DRAWINGS

Figure 1:
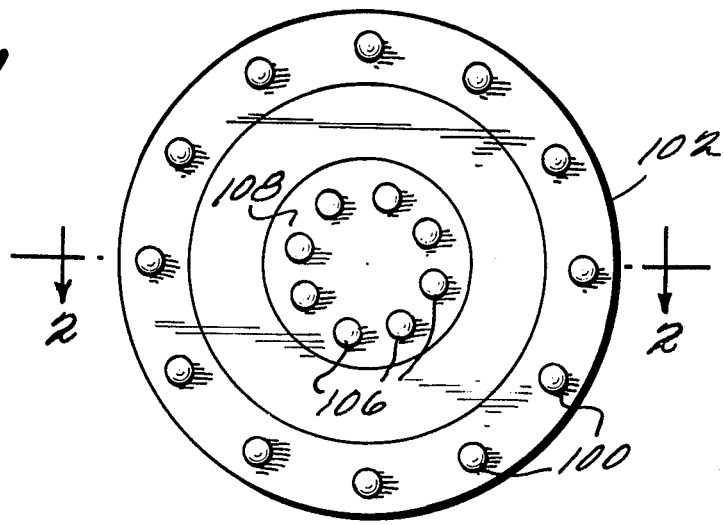
FIG. 1 shows a top plan view of one embodiment of the sensor of the present invention.
Figure 2:
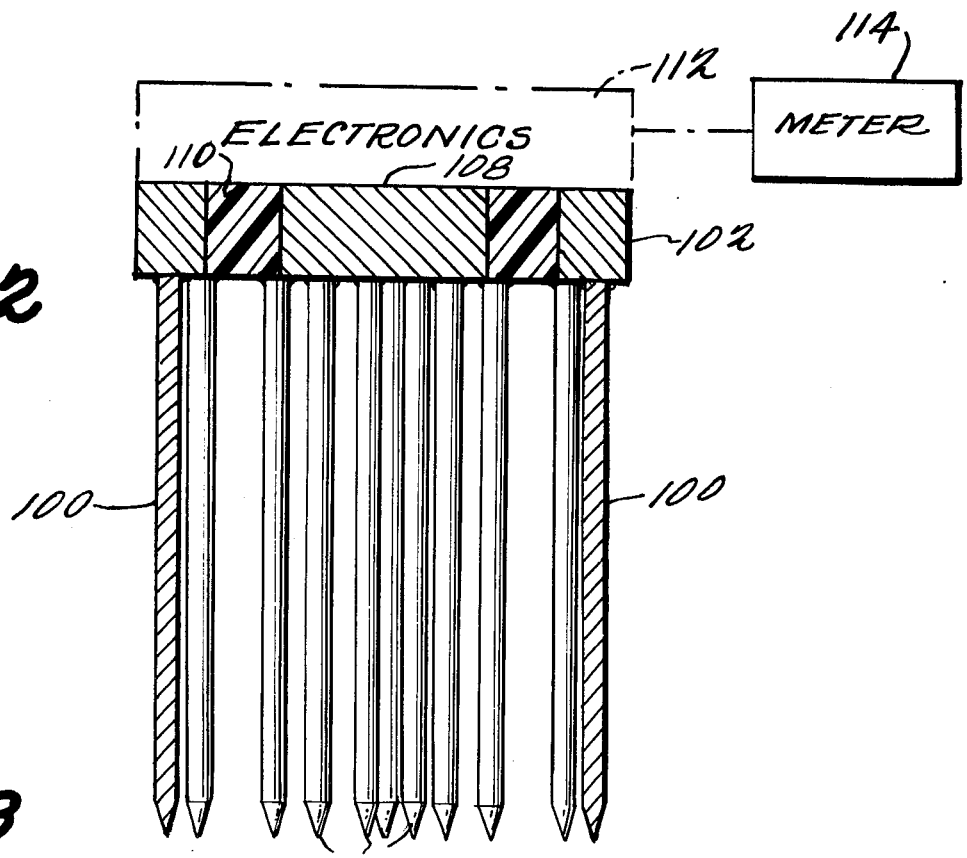
FIG. 2 shows a sectional view of the sensor of FIG. 1 along the lines 2—2 of FIG. 1.

Reference is now made to FIGS. 1 and 2 which illustrate one embodiment of the soil sensor of the present invention. In this embodiment, a first ring of spines, for example, stainless steel spines 1/16 inch in thickness and several inches in length form a first ring 100 attached to and extending outwardly from a metallic annular ring 102, formed, for example, of brass or other material. The spines or ring 100 can be attached to the annular ring 102 in any suitable fashion. A second ring of spines 106 extend outward from a center metal ring 108 also of brass or any other suitable material. The spines of rings 100 and 106 thus extend outward in parallel to each other and are pointed on the ends remote from the base formed by rings 102, 108) and 110. Rings 102 and 108 are separated and held together with an annular ring 110 of electrically insulating material, for example, polyethylene. Electronic circuit 112 provides an output signal to meter 114, indicating the moisture content of material into which the sensor is inserted and is mounted atop rings 102 and 108. Enough spines should be used so that the spines appear like a ground plane, but are still readily insertable in the material to be tested.

Figure 3:
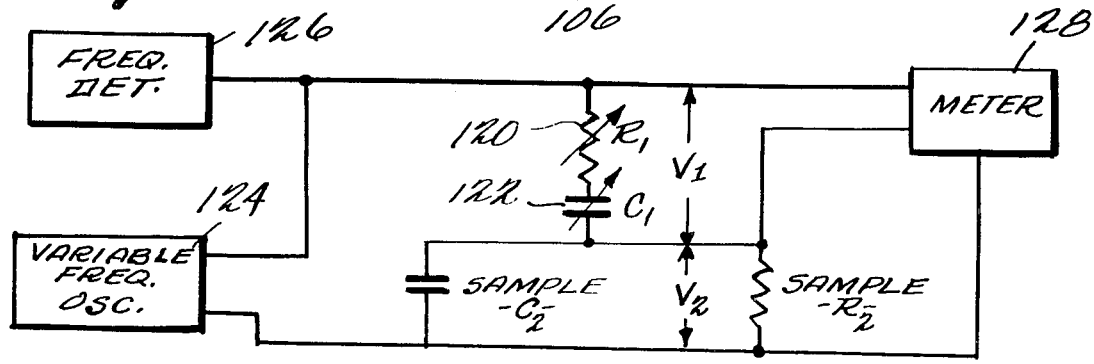
FIG. 3 shows an electrical schematic of the circuitry and material impedance measured by the present invention.

FIG. 3 shows one circuit for producing signals which can be utilized to determine moisture content. Variable resistance 120 and capacitance 122 combine with the capacitance and resistance of the material into which the probe is inserted to form a Wien bridge. The bridge is coupled to a conventional variable frequency oscillator 124 and the bridge is utilized conventionally to determine both the resonant frequency by way of a frequency detector 126 and the voltage ratio by way of meter 128. The resonant frequency W is determined by the following relation:

$$W^2 = (1/R_1 R_2 C_1 C_2)$$

wherein:

$R_1$ and $C_1$ are the resistance and capacitance, respectively, of the bridge elements; and, $R_2$ and $C_2$ are the resistance and capacitance, respectively, of the material.

The voltage ratio is determined by the following relation:

$$\frac{V_2}{V_1} = \frac{1}{1 + \frac{C_2}{C_1} + \frac{R_1}{R_2}}$$

Solving these two equations, either manually with the aid of a calculator, or automatically by a micro-processor or otherwise, gives the capacitance and resistance of the sample, and these figures can then be easily used to calculate the dielectric constant. The dielectric constant can then be related to the moisture content using known relations.

In materials where the resistance is very large, for example, trees, it may be possible to ignore the resistance value and accordingly only the resonant frequency would need to be measured. In such an application, it may also be desirable to add another resistance and capacitance in parallel with the capacitance and resistance provided by the material to provide wider control of the operating frequency. As an alternative to utilizing a separate oscillator, a conventional Wien bridge oscillator can be utilized in such circumstances where resistance can be ignored. By variation of the frequency, a considerable range of frequencies can be examined to accurately determine the dispersive properties of the material.

If desired, to determine the rate of penetration of moisture through a material several probes can be inserted in parallel at different levels of the material.

Many changes and modifications can, of course, be made in the above-described embodiment of the invention. Accordingly, that embodiment is intended to be limited only by the scope of the appended claims.

What is claimed is:

1. A moisture sensor comprising:
   a base,
   a first ring of spines extending outwardly from said base in parallel;
   a second ring of spines extending outwardly from said base in parallel within said first ring, separated and electrically insulated therefrom, said spines being sufficient in number to appear as a ground plane forming an effective coaxial capacitor and being insertable into material to be sensed; and
   circuit means connected to said first and second rings for applying an ac signal to said spines measuring the impedance of said material between said rings.

2. A moisture sensor comprising:
   a probe having a base, a first ring of spines extending outwardly from said base in parallel, a second ring of spines extending outwardly from said base in parallel within said first ring, means electrically insulating said first ring from said second ring, said rings being sufficient in number to appear as a ground plane forming an effective coaxial capacitor and being insertable into material to be sensed;
   circuit means including an RC bridge with a resistor and capacitor connected to said first and second rings for applying an ac signal to said spines to form a bridge with the resistance and capacitance of said material between said rings, for producing electrical signals indicating the impedance of said materials;
   means for producing a variable frequency signal and applying said signal to said bridge; and
   meter means connected to said bridge for indicating voltage.

3. A sensor as in claim 1 or 2 wherein said circuit means is mounted on said base on the side opposite the side from which said spines extend.

4. A sensor as in claim 1 or 2 wherein said spines are stainless steel.